United States Patent

Roskott et al.

[11] 4,052,465
[45] Oct. 4, 1977

[54] PREPARATION OF ORGANIC PEROXIDES

[75] Inventors: Lodewijk Roskott, Gorssel; Arnold Schroeder, Deventer, both of Netherlands

[73] Assignee: Akzona, Incorporated, Asheville, N.C.

[21] Appl. No.: 425,856

[22] Filed: Dec. 18, 1973

[30] Foreign Application Priority Data

Dec. 22, 1972    United Kingdom ............... 59395/72

[51] Int. Cl.$^2$ .................... C07C 179/02; C07C 179/06
[52] U.S. Cl. ............................... 260/610 R; 260/861; 260/42 R; 260/339; 560/190
[58] Field of Search ........ 260/610 R, 610 SC, 610 A, 260/339, 473 R, 484 R, 484 P

[56] References Cited

U.S. PATENT DOCUMENTS

| | | | |
|---|---|---|---|
| 3,003,000 | 10/1961 | Milas | 260/610 C |
| 3,149,126 | 9/1964 | Milas | 260/338 |
| 3,652,717 | 3/1972 | Gerritsen | 260/610 C |
| 3,668,139 | 6/1972 | Daniels et al. | 260/610 C |

*Primary Examiner*—Bernard Helfin
*Assistant Examiner*—W. B. Lone

*Attorney, Agent, or Firm*—Stevens, Davis, Miller & Mosher

[57] ABSTRACT

A process for the polymerization of vinyl or vinylidene-group-containing esters in the presence of a free radical generating compound as an initiator and a metal compound as an accelerator comprising, as an initiator, an organic peroxidic composition consisting essentially of a compound having the general formula

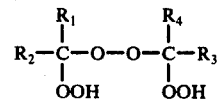

wherein $R_1$, $R_2$, $R_3$ and $R_4$ may be the same or different and each represents hydrogen, branched or unbranched alkyl, if desired substituted by hydroxy, alkoxy, alkoxycarbonyl or halogen, aryl, if desired substituted by alkyl, hydroxy, alkoxy or halogen, or aralkyl wherein the aryl group may be substituted by alkyl, hydroxy, alkoxy or halogen, and wherein $R_1$ together with $R_2$, $R_3$ together with $R_4$, and $R_1$ together with $R_4$ form a branched or unbranched alkylene group, and $R_1$ together with $R_2$ and $R_3$ form a branched or unbranched alkylylidene group.

10 Claims, No Drawings

PREPARATION OF ORGANIC PEROXIDES

The present invention relates to the peroxidic polymerization or copolymerization of vinyl or vinylidene-group-containing esters, to the preparation of an organic peroxidic composition for use in said polymerization or copolymerization, and to an organic peroxidic composition per se.

Unsaturated esters may be prepared by condensation of α,β-unsaturated monocarboxylic acids, such as acrylic or methacrylic acids with mono-, di- or polyhydric alcohols. As examples of these alcohols, there may be mentioned as monohydric alcohols: methanol, ethanol, iso-propanol, cyclohexanol and phenol; as dihydric alcohols: ethylene glycol, propylene glycol, 2,2-bis(4-hydroxyphenyl)propane, 2,2-bis(4-hydroxycyclohexyl)-propane and 2,2-bis(4-β-hydroxyethyloxyphenyl)propane; and as polyhydric alcohols: pentaerythritol and its dimers, trimethylol-propane and glycerol. Further there may be mentioned the complex diols or polyols described in Dutch patent application 6808040, German "Auslegeschrift" No. 1,645,379, U.S. Pat. Nos. 2,895,950 and 2,628,178, British Pat. Nos. 928,307 and 956,826 and French Pat. 1,404,000.

Unsaturated esters may also be obtained by reacting α,β-unsaturated monocarboxylic acids with compounds which contain epoxy groups like phenyl glycidyl ether and bisphenol A bisglycidyl ether.

The hereinbefore described ethylenically unsaturated esters, which may be characterized by having terminal $>C=C<$ groups, may be homopolymerized or copolymerized in the presence of free radical generating compounds or compositions. As copolymerizable monomers may be considered vinyl monomers, such as styrene, p-chloro-styrene, α-methyl-styrene, methylmethacrylate, methylacrylate, di-n-butylitaconate or vinyl-toluene.

The polymerization or copolymerization is preferably carried out at ambient temperatures; in that case, the free radical generating compound or composition has to be used in combination with an accelerator. It has already been proposed to use a combination of a ketone peroxide, e.g. methylethylketone peroxide, as an initiator and a cobalt salt as an accelerator in the polymerization of unsaturated esters derived from α,β-unsaturated acids and mono-, di- or polyhydric alcohols or in the copolymerization of such esters with vinyl monomers at ambient temperature. This combination, however, is ineffective, as is demonstrated by a long gel time and a slow cure. In some cases, the use of a co-accelerator, e.g. tertiary amines, is recommended as an improvement. However, such a co-accelerator causes an unwanted discoloration of the finished polymers or copolymers. Moreover, the mixture of initiator and accelerator gives rise to a severe foaming due to gas development.

It is therefore an object of the invention to provide a process for polymerizing or copolymerizing ethylenically unsaturated esters which is devoid of the foregoing disadvantages. Another object of the invention is to provide a process for polymerizing or copolymerizing esters which contain a vinyl or vinylidene group which does not require undesirably long gel and cure times and produces polymers which are not undesirably discolored. Still another object of the invention is to provide a novel peroxidic initiator composition for polymerization and copolymerization of unsaturated esters.

Surprisingly, it has now been found that an organic peroxidic composition consisting essentially of a compound having the general formula

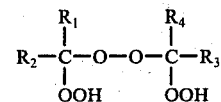

wherein $R_1$, $R_2$, $R_3$ and $R_4$ may be the same or different and each represents hydrogen, branched or unbranched alkyl, if desired substituted by hydroxy, alkoxy, alkoxycarbonyl or halogen, aryl, if desired substituted by alkyl, hydroxy, alkoxy or halogen, or aralkyl wherein the aryl group may be substituted by alkyl, hydroxy, alkoxy or halogen, and wherein $R_1$ together with $R_2$, $R_3$ together with $R_4$, and $R_1$ together with $R_4$ form a branched or unbranched alkylene group, and $R_1$ together with $R_2$ and $R_3$ form a branched or unbranched alkylylidene group, in conjunction with a transition metal salt, is an effective initiator for the polymerization or copolymerization of vinyl or vinylidene-group-containing esters.

Any suitable peroxide of the above formula may be used in practicing the invention, including, for example:
1. 2,5-dimethyl-2,5-dihydroperoxy-3,4-dioxahexane,
2. 3,6-dimethyl-3,6-dihydroperoxy-4,5-dioxaoctane,
3. 3,6-diethyl-3,6-dihydroperoxy-4,5-dioxaoctane,
4. 2,4,7,9-tetramethyl-4,7-dihydroperoxy-5,6-dioxadecane,
5. 2,4,7,9-tetramethyl-2,9-dihydroxy-4,7-dihydroperoxy-5,6-dioxadecane,
6. 2,4,7,9-tetramethyl-2,9-dimethoxy-4,7-dihydroperoxy-5,6-dioxadecane,
7. 1,4-diphenyl-1,4-dihydroperoxy-2,3-dioxabutane,
8. 1,4-bis(p-methoxyphenyl)-1,4-dihydroperoxy-2,3-dioxabutane,
9. 1,1'-dihydroperoxy-1,1'-bis(2,6-dimethylcyclohexyl) peroxide;
10. 1,1'-dihydroperoxy-1,1'-dicyclohexylperoxide,
11. 1,1'-dihydroperoxy-1,1'-bis(3-methylcyclohexyl)peroxide,
12. 1,1'-dihydroperoxy-1,1'-bis(4-methylcyclohexyl)peroxide,
13. 1,1'-dihydroperoxy-1,1'-bis(3,3,5-trimethylcyclohexyl)peroxide,
14. 1-(2'-hydroperoxy-2'-butylperoxy)-cyclohexyl-1-hydroperoxide,
15. 2,4,7,9-tetramethyl-2,9-diphenyl-4,7-dihydroperoxy-5,6-dioxadecane,
16. 1,1'-dihydroperoxy-1,1'-dicyclopentylperoxide,
17. 1,1'-dihydroperoxy-1,1'-bis(3-methylcyclopentyl)peroxide,
18. 2,5-bis(ethoxycarbonylmethyl)-2,5-dihydroperoxy-3,4-dioxahexane;
19. 1,8-bis(ethoxycarbonyl)-3,6-dimethyl-3,6-dihydroperoxy-4,5-dioxaoctane,
20. 4,7-dihydroperoxy-5,6-dioxadecane,
21. 2,7-dimethyl-3,6-dihydroperoxy-4,5-dioxaoctane,
22. 1,6-diphenyl-2,5-dimethyl-2,5-dihydroperoxy-3,4-dioxahexane,
23. 3,5-dimethyl-3,5-dihydroperoxy-1,2-dioxolane,
24. 3-methyl-5-phenyl-3,5-dihydroperoxy-1,2-dioxolane,
25. 3,5-diphenyl-3,5-dihydroperoxy-1,2, -dioxolane,
26. 3,6-dimethyl-3,6-dihydroperoxy-1,2-dioxane,
27. 5-methyl-2-phenyl-2,5-dihydroperoxy-3,4-dioxahexane, 28. 3-methyl-4,5-cyclotetramethylene-3,5-dihydroperoxy-1,2-dioxolane,
29. bis(2,6-dimethyl-4-hydroperoxyheptyl)-4,4'-peroxide,
30. bis(5-methyl-3-hydroperoxyheptyl)-3,3'-peroxide,
31. 7,10-dihydroperoxy-8,9-dioxahexadecane,
32. 2,5,8,11-tetramethyl-5,8-dihydroperoxy-6,7-dioxadodecane,
33. 1,1,6,6-tetrachloro-2,5-dihydroperoxy-3,4-dioxahexane,
34. 3,8-diethyl-4,7-dihydroperoxy-5,6-dioxadecane,
35. 2,2,7,7-tetramethyl-3,6-dihydroperoxy-4,5-dioxa-1,8-octane diol,
36. 1,4-bis(4'-chlorophenyl)-1,4-dihydroperoxy-2,3-dioxabutane,
37. 1,1-bis(2'-chlorophenyl)-1,4-dihydroperoxy-2,3-dioxabutane,
38. 12,15-dihydroperoxy-13,14-dioxa-hexacosane, and
39. 1,6-diphenyl-2,5-dihydroperoxy-3,4-dioxahexane.

The foregoing peroxides are referred to hereinafter by number and have the following formulae:

(1) 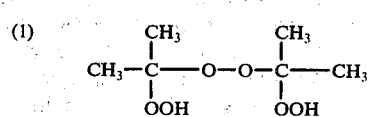

(2) 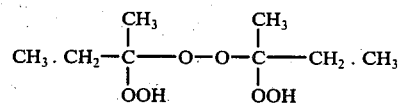

(3) 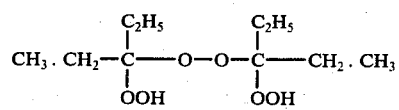

(4) 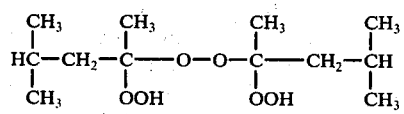

(5) 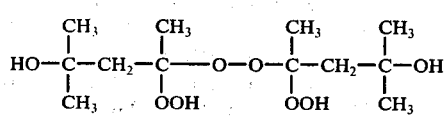

(6) 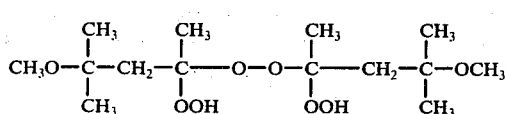

(7) 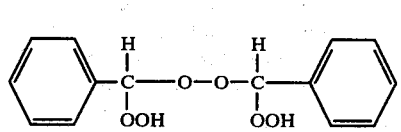

(8) 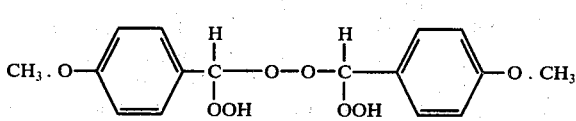

(9) 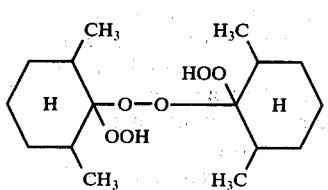

(10) 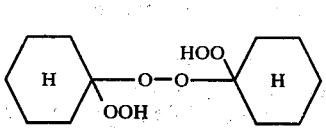

(11) 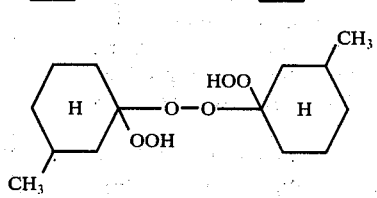

-continued
(12) 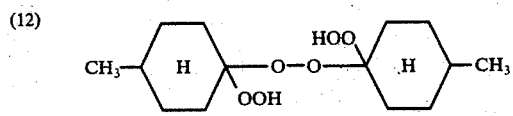
(13) 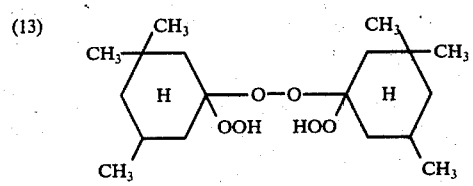
(14) 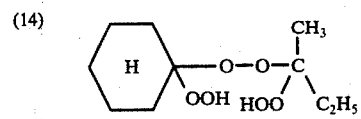
(15) 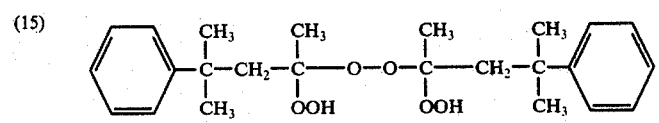
(16) 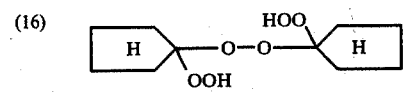
(17) 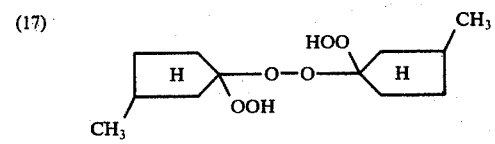
(18) 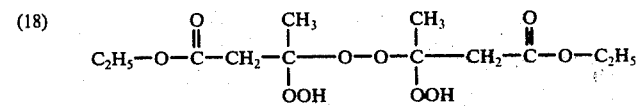
(19) 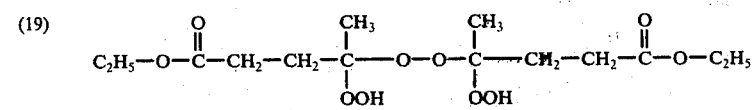
(20) 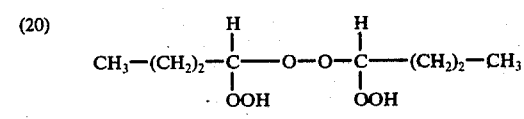
(21) 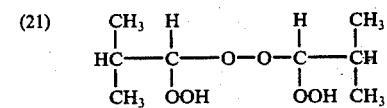
(22) 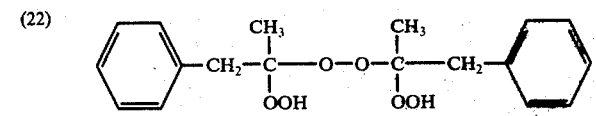
(23) 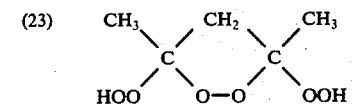
(24) 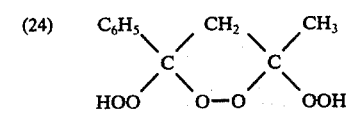
(25) 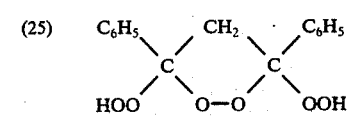

-continued
(26) 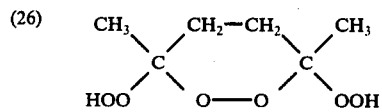
(27) 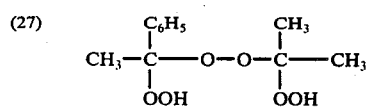
(28) 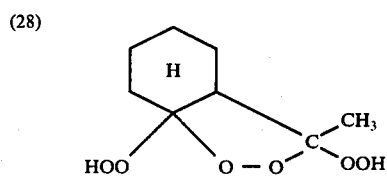
(29) 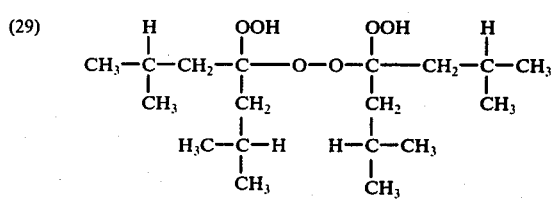
(30) 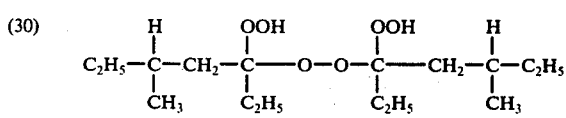
(31) 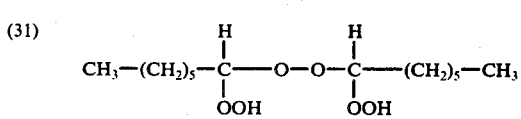
(32) 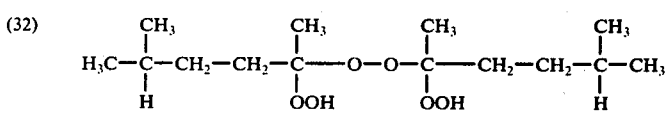
(33) 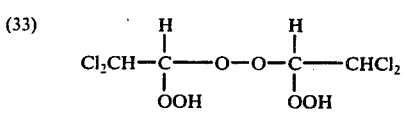
(34) 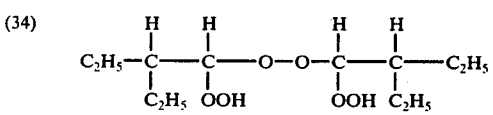
(35) 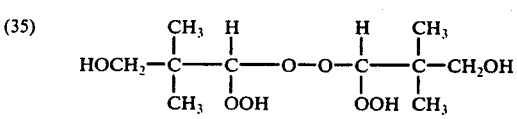
(36) 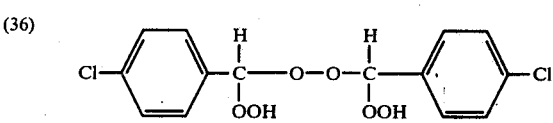
(37) 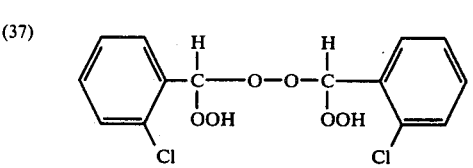
(38) 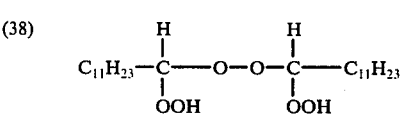

(39) 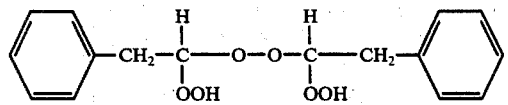

The above list of peroxides is given only as examples and other peroxides of formula (1) may be used.

The peroxidic compositions to be used according to the invention may be incorporated into the esters to be polymerized or copolymerized either as such or preferably, for considerations of safety, after incorporating the peroxidic compositions into one or more plasticizers and/or phlegmatizers and/or solid carriers and/or low or high boiling solvents. The peroxidic compositions may be incorporated not only in the form of solutions but also in the form of pastes or putties.

As plasticisers and/or phlegmatisers and/or solvents may be used esters such as dialkyl phthalates, the alkyl group-containing 1–10 C-atoms including ring structures, ethyl acetate, butyl acetate, trialkyl or triaryl phosphates, hydrophylic solvents such as mono- or polyhydric alcohols, di- or triethylene glycols, certain ketones and hydroxy or alkoxy ketones such as diacetone alcohol, hydrophobic solvents such as benzene, toluene, xylene or aliphatic hydrocarbons.

The peroxidic compositions to be used according to the invention may be incorporated into the esters to be (co)polymerised in amounts of 0.1–10% by weight, calculated on the esters to be (co)polymerised.

It is also recommendable to incorporate the peroxides according to the invention into fillers such as clay, calcium carbonate, or silica. It may be advantageous to add to the peroxidic composition flame-retarding or suppressing agents, stabilisers such as mono- or dipicolinic acid, pyrophosphates, alumina compounds, (poly)ethylene glycol ethers, pyrrolidone, N-methyl pyrrolidone, polyvinyl pyrrolidone, aliphatic or hydroxy aliphatic amines, sequestering or masking agents such as nitrilotriacetic acids.

For carrying out the polymerisation or copolymerisation at ambient temperature, use has to be made of transition metal salts, such as halides or acylates derived from cobalt, iron, copper, vanadium, cerium, manganese, tin, silver and mercury, preferably from cobalt, manganese and vanadium. These salts have to be incorporated in amounts ranging from 0.001 to 0.5%, preferably 0.005 to 0.05% calculated as metal by weight of the polymerisable material.

It is observed that in the British Pat. No. 840,838 the preparation of 1.1'-dihydroperoxy-dicyclohexyl peroxide is described, by adding cyclohexanone to a mixture of hydrogen peroxide and diluted nitric acid. The use of this method for preparing peroxides has some drawbacks. Most of the dihydroperoxy peroxidic compounds as represented by formula I are not completely soluble in water. Generally such peroxidic compounds are dangerous materials, e.g. very impact sensitive, and therefore they must be phlegmatised with inorganic or organic materials. For purposes of safety, this phlegmatiser must already be present during the preparation of the peroxidic compound. However, by carrying out the process as described in the above British patent in the presence of a phlegmatiser, a monomeric peroxide is obtained which may be represented by the chemical structure

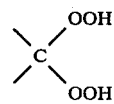

This monomeric peroxide, prepared in e.g. hexylene glycol as a phlegmatiser, may be obtained water-free by distilling off the water present after the reaction has been finished.

According to another ambodiment of the present invention, it has now been found that the peroxidic composition for use as an initiator in the polymerisation or copolymerisation of vinyl or vinylidene-group-containing esters may be prepared by an acid catalysed reaction between carbonyl compounds with the general formulae:

$$\begin{array}{c} R_1 \\ \diagdown \\ \diagup \\ R_2 \end{array} C=O \quad \text{and} \quad \begin{array}{c} R_3 \\ \diagdown \\ \diagup \\ R_4 \end{array} C=O$$

in which the symbols R have the meanings as hereinbefore defined, and hydrogen peroxide in the presence of a solvent in which both the starting carbonyl compounds and the peroxidic composition formed are substantially soluble under simultaneous removal of water by distillation.

In the above process the peroxidic composition as defined is prepared safely. Moreover, the presence of a suitable solvent increases the velocity of the reaction, and consequently shortens the reaction time. Finally the presence of a solvent makes the removal of the acid catalyst easier. In carrying out the reaction while simultaneously removing water by distillation, a peroxidic composition is formed consisting essentially of a compound with the general formula I and therefore pre-eminently suited for use as an initiator in the process according to the present invention. Illustrative examples of starting carbonyl compounds are acetone, methyl ethyl ketone, diethyl ketone, methylisobutyl ketone, di-isobutyl ketone, cyclohexanone, alkyl substituted cyclohexanones, cyclopentanone, alkyl substituted cyclopentanones, aromatic substituted aliphatic ketones, β- or γ-diketones such as acetylacetone, benzoyl acetone or acetonyl acetone, diacetone alcohol, 2-methyl-2-methoxy pentanone-4, benzaldehyde, methoxy-benzaldehyde, branched or unbranched aliphatic aldehydes, aceto acetic acid esters, laevulinic acid esters, ethyl isoamyl ketone, di-isoamyl ketone, 5-methyl hexanone-2, hydroxy- or chloro-substituted branched or unbranched aliphatic aldehydes, chloro-benzaldehyde.

The solvent used in the preparation process may be the same substance as suited to phlegmatise the peroxidic composition. Alternatively, e.g. if the phelematising substance desired is not suited for carrying out the preparation process, another solvent may be used. In the latter case it is recommended to add the phlegmatiser after the peroxidic composition has been formed, however, before removing the solvent used e.g. by distillation.

The solvents used in the preparation process may preferably be selected from benzene, toluene, butylacetate and other liquids which form an azeotrope with water.

The distillation is preferably carried out under reduced pressure. The preparation is carried out at a temperature of 10°-50° C, preferably at 20°-40° C. The hydrogen peroxide is used as a solution in water having a $H_2O_2$ content varying from 30–85% w/w, preferably from 50–70% w/w. The carbonyl compounds are used in such a total amount that the molar ratio of carbonyl groups to $H_2O_2$ is between 1:1.0 and 1:4.0, preferably between 1:1.5 and 1:2.2.

The acid catalyst is selected from mineral acids, such as sulfuric acid, phosphoric acid and nitric acid, strong acid ion exchangers and strong organic acids, such as benzene and toluene sulfonic acid, chloro-substituted acetic acid, formic acid, and is used in an amount of 0.2–200 mg. equivalent per mole of the carbonyl compounds, preferably 2–50 mg. equivalent. After the reaction the acid catalyst is removed by washing with an aqueous alkaline solution containing alkali hydrogen carbonate, alkali hydroxide or alkali carbonate, by adding a calcium or magnesium oxide or -carbonate followed by a filtration or by a simple filtration when an ion exchanger is used.

Preferably, after the addition of a suitable phlegmatiser such as dialkyl phthalates, trialkyl phosphates, alkylene glycols, alkylene glycol monoor diethers, diethyleneglycols, diethyleneglycol mono- or diethers, alkylene or dialkyleneglycol mono ether esters, higher boiling alcohols like dodecanol, octyl or nonylalcohol, cyclohexanol, Diacetone alcohol, hexylene glycol, polyethylene glycol (M.W. <2000), hexamethylene glycol, 1.4-butyleneglycol, neopentylglycol, 2-pyrrolidone or n-methyl-2-pyrrolidone, the lower boiling solvent used in the preparation is removed, preferably by distillation, provided that this solvent is different from the above phlegmatiser. A solvent of a peroxidic composition is obtained having an active oxygen content between 2 and 12%, the major part of the active oxygen being present in the form of a peroxidic compound of formula I.

In order to increase in the peroxidic composition the content of a peroxidic compound of formula (1), an after-treatment is employed, if desired, with a solution of sodium sulfite in water. Surprisingly, it has been found that other peroxidic components present as by-products in the peroxidic composition, are selectively reduced by this treatment. By using the process according to the invention novel organic peroxidic compositions may be obtained consisting essentially of a compound mentioned in the list hereinbefore under Nos. 4, 5, 6, 7, 8, 9, 13, 14, 15, 17, 18, 19, 20, 21, 22, 24, 25, 27, 28, 29, 30, 31, 32, 33, 34, 35, 36, 37, 38 and 39.

The following examples illustrate the invention, but are not to be construed as limiting the scope thereof. The peroxides used in these examples are added to the resin or resin mixtures in such an amount that each sample contains 0.105% of active oxygen. In some examples, this amount is doubled. The accelerator used consists of a solution of cobalt octoate in dioctyl phthalate having a cobalt content of 1% by weight. The gel times are determined with 10 g of samples in a thermostatted bath at 20° C. The cure obtained was determined by means of a Peroz pendulum hardness meter on unfilled, non-reinforced layers having a thickness of 1 mm and covered during the cure with tin-foil in order to avoid air-inhibition and evaporation of styrene monomer.

All determinations were carried out twice, the values mentioned are the arithmetic average of both determinations. The various resin types used are abbreviated as follows:

A = the condensation product of 1 mole methacrylic acid and 1 mole methanol,

B = the condensation product of 2 moles acrylic acid and 1 mole bisphenol A bis glycidyl ether, and C = the condensation product of 2 moles methacrylic acid and 1 mole bisphenol A bis($\beta$-hydroxyethylether). Both the condensation products B and C have two terminal double bonds per molecular unit.

EXAMPLE I

A composition consisting of 55 parts of product B and 45 parts of styrene was mixed with a peroxide to be used according to the invention and cobalt octoate. After mixing, the geltime and curing were determined as described. The peroxides used and the data obtained are tabulated hereafter.

| peroxide No. | amount % w/w | cobalt octoate % w/w | geltime at 20° C/min. | Persoz hardness after 6 hours at 20° C |
|---|---|---|---|---|
| 2 | 0.92 | 1.0 | 20 | 191 |
| 2 | 0.92 | 2.0 | 17 | 194 |
| 4 | 1.16 | 1.0 | 32 | 174 |
| 4 | 1.16 | 2.0 | 24 | 186 |
| 10 | 1.14 | 1.0 | 19 | 184 |
| 10 | 1.14 | 2.0 | 17 | 188 |
| 12 | 1.26 | 1.0 | 33 | 156 |
| 12 | 1.26 | 2.0 | 24 | 165 |
| 20 | 1.75 | 0.5 | 15 | 217 |
| 20 | 1.75 | 1.0 | 10 | 222 |
| 20 | 3.50 | 0.5 | 8 | 245 |
| 20 | 3.50 | 1.0 | 6 | 244 |
| 21 | 1.63 | 0.5 | 14 | 214 |
| 21 | 1.63 | 1.0 | 10 | 223 |
| 21 | 3.26 | 0.5 | 8 | 238 |
| 21 | 3.26 | 1.0 | 5 | 244 |
| 23 | 1.36 | 0.5 | 78 | 119 |
| 23 | 1.36 | 1.0 | 38 | 152 |
| 23 | 2.72 | 0.5 | 21 | 161 |
| 23 | 2.72 | 1.0 | 12 | 179 |
| 1 | 1.0 | 1.0 | 22 | 185 |
| 1 | 2.0 | 1.0 | 13 | 206 |
| 14 | 1.0 | 1.0 | 21 | 190 |
| 14 | 2.0 | 1.0 | 12 | 214 |
| 30 | 1.5 | 0.5 | 109 | 19 |
| 30 | 1.5 | 1.0 | 84 | 81 |
| 29 | 1.5 | 0.5 | 102 | 123 |
| 29 | 1.5 | 1.0 | 108 | 119 |

EXAMPLE II

Product C was mixed with a peroxide according to the invention and cobalt octoate. Subsequently, geltime and curing were determined as described. The peroxides used and the data obtained are tabulated below.

| peroxide No. | amount % w/w | cobalt octoate % w/w | geltime at 20° C/min. | Persoz hardness after 6 hours at 20° C. |
|---|---|---|---|---|
| 2 | 0.92 | 1.0 | 33 | 127 |
| 2 | 0.92 | 2.0 | 33 | 153 |
| 4 | 1.16 | 1.0 | 88 | 93 |
| 4 | 1.16 | 0.5 | 112 | 70 |
| 4 | 2.32 | 1.0 | 60 | 112 |
| 4 | 2.32 | 0.5 | 73 | 85 |
| 10 | 1.14 | 1.0 | 19 | 119 |
| 10 | 1.14 | 2.0 | 16 | 152 |
| 20 | 1.75 | 1.0 | 64 | 98 |
| 20 | 1.75 | 0.5 | 78 | 77 |
| 20 | 3.50 | 1.0 | 31 | 95 |

-continued

| peroxide | | cobalt octoate % w/w | geltime at 20° C/min. | Persoz hardness after 6 hours at 20° C. |
|---|---|---|---|---|
| No. | amount % w/w | | | |
| 20 | 3.50 | 0.5 | 40 | 82 |
| 21 | 1.63 | 1.0 | 98 | 31 |
| 21 | 1.63 | 0.5 | 117 | 26 |
| 21 | 3.26 | 1.0 | 74 | 88 |
| 21 | 3.26 | 0.5 | 87 | 78 |
| 31 | 1.5 | 1.0 | 52 | 106 |
| 31 | 3.0 | 0.5 | 43 | 98 |

EXAMPLE III

Product A was mixed with a peroxide to be used according to the invention and with cobalt octoate. The peroxide was added in a quantity of active oxygen corresponding with 2 m.mol of peroxide per 100 g of product A. The conversion was determined with the aid of a dilatometer. The peroxides used and the data obtained are tabulated hereafter.

| peroxide | | cobalt octoate sol. 1% w/w Co | 40% conversion at 20° C after hours |
|---|---|---|---|
| No. | amount m.mol/100g product | | |
| 10 | 2 | 0.46 | 25 |
| 30 | 2 | 0.46 | 28 |
| 2 | 2 | 0.46 | 36 |
| 31 | 2 | 0.46 | 24 |

EXAMPLE IV

A product was mixed with a peroxide to be used according to the invention. To this mixture a solution of pentavalent vanadium in monobutyl phosphite was added. The geltime and curing were determined as described. The products and peroxides used and the data obtained are tabulated below.

| pro-duct | peroxide | | metal accelerator | | geltime at 20° C/min. | Persoz hardness after 6 hours at 20° C. |
|---|---|---|---|---|---|---|
| | No. | amount % w/w | | % w/w | | |
| B | 10 | 1.14 | V$^{5+}$ | 0.0028 | 12 | 219 |
| B | 10 | 2.28 | V$^{5+}$ | 0.0028 | 10 | 235 |
| B | 10 | 1.14 | V$^{5+}$ | 0.0056 | 11 | 221 |
| C | 2 | 0.92 | V$^{5+}$ | 0.0028 | 7 | 164 |
| C | 2 | 0.92 | V$^{5+}$ | 0.0056 | 6 | 188 |
| C | 2 | 1.84 | V$^{5+}$ | 0.0028 | 4 | 182 |

EXAMPLE V 38.9 g of hydrogen peroxide solution 70% w/w (0.8 mole) were added to a mixture of 30 ml benzene, 43 g (0.5 mole) of diethylketone and 0.17 g of p-toluene sulfonic acid (2 mg eq./mole ketone) in 15 minutes. By cooling the temperature was kept at 20° C. After the addition had been completed, about 19 g of water were removed from the reaction mixture by azeotropic distillation under reduced pressure at 30° C. The atmospheric pressure was restored and then 40 ml of water were added and the pH of the mixture was adjusted to about 5.5 with a 2N.NaOH solution. After stratification the water layer was removed by separation. 31 g of diisobutyl phthalate were added to the organic layer and benzene was distilled off under reduced pressure. 86 g of peroxide solution was obtained with a total active oxygen (AO) content of 13.6%. About 70% of the active oxygen was present in the form of the dihydroperoxyperoxide No. 3, the remainder was constituted of a trace of hydrogen peroxide and 3.3-dihydroperoxypentane (thin layer chromatography). The solution obtained can be used as such, but preferably the impurities mentioned above are removed by a selective reduction. This reduction includes a treatment with a concentrated sodium sulphite solution at room temperature, followed by washing with water. The resulting solution (71 g; AO content 11.4%) was diluted with 19 g of a diacetone alcohol to give 90 g of peroxide solution with an AO content of 9.0%.

EXAMPLE VI 38.9 g of H$_2$O$_2$ 70% w/w (0.8 mole) were added to a mixture of 30 ml of benzene, 64 g (0.5 mole) of ethyl isoamyl ketone and 1 ml of 2N sulfuric acid (2 mg. eq./mole ketone) at 20° in 15 minutes. Subsequently, water was removed from the reaction mixture by azeotropic distillation at 25°-30° C under reduced pressure. After the distillation had been completed, 0.5 g of magnesium sulfate and 0.2 g of magnesium carbonate were added and the mixture was stirred during 30 minutes and filtered. 25 g of dimethylphthalate were added to the filtrate. Then benzene was removed by distillation under reduced pressure at 25° C. 100 g of peroxide solution was obtained with a total AO content of 11.5%. By thin layer chromatographicanalysis it was demonstrated that 85% of the AO is present in the form of peroxide No. 30.

By selective sulfite reduction as described in example V the other peroxide formed as a by-product, viz. 3.3-dihydroperoxy-5-methylheptane was removed, giving 91 g of purified product with a total AO content of 10.7%. This product contained substantially one single peroxide, viz. No. 30. By adding 44 g of triethylphosphate the active oxygen content was reduced to 7.2%.

In an analogous way, solutions of the following peroxides were prepared, starting from various ketones:

| peroxide No. | starting from |
|---|---|
| 1 | acetone |
| 2 | methyl ethyl ketone |
| 4 | methyl isobutyl ketone |
| 5 | diacetone alcohol |
| 6 | 2-methoxy-2-methyl-4-pentanone |
| 9 | 2.6-dimethylcyclohexanone |
| 11 | 3-methylcyclohexanone |
| 12 | 4-methylcyclohexanone |
| 13 | 3.3.5-trimethylcyclohexanone |
| 15 | 2-methyl-2-phenyl-4-pentanone |
| 16 | cyclopentanone |
| 17 | 3-methylcyclopentanone |
| 18 | ethyl acetoacetate |
| 19 | ethyl laevulinate |
| 22 | phenyl acetone |
| 23 | acetyl acetone (2.4-pentadione) |
| 24 | benzoyl acetone (1-phenyl-1.3-butadione) |
| 25 | dibenzoyl methane (1.3-diphenyl-1.3-propadione) |
| 26 | acetonyl acetone (2.5-hexadione) |
| 27 | acetophenone |
| 28 | 2-acetylcyclohexanone |
| 29 | diisobutylketone |
| 32 | methyl isoamyl ketone. |

EXAMPLE VII 2.5 g of a strong acid ion exchanger (trade name Dowex 50 W; 4 mg.eq.acid/g substance) and 53.6 g of 70% w/w hydrogen peroxide solution (1.1 mole) were added to 50 g of diisobutyl phthalate. The reactor was flushed with nitrogen. Then 60.4 g of heptanal (purity 94.3%) (0.5 mole) were added in 15 minutes. By cooling, the temperature was kept at 20° C during the addition and during stirring for 1 hour. Subsequently, the rector was connected to a vacuum system and water was slowly distilled from the reaction mixture at 20° C. In 4 hours 31 g of water containing 6.8 g of $H_2O_2$ was distilled off together with 1 g of aldehyde. After the ion exchanger had been removed by filtration, 136 g of peroxide solution was obtained with a total AO content of 10.6%, the major part being dihydroperoxyperoxide No. 31. After mixing with 100 ml of hexane, the bulk of peroxide No. 31 crystallised at 0° C. After filtration and washing with fresh hexane, a purified peroxide was obtained have a melting point of 61°–62° C; AO content 15.8%; purity 97% (T.L.C.). The infrared spectrum showed a strong band at 3438 cm$^{-1}$ due to O—O—H.

100 g of the above peroxide solution with an AO content of 10.6% were diluted with 71 g of diethylene glycol to produce a solution with an AO content of 6.2%.

In an analogous way, solutions of the following peroxides were prepared, starting from various aldehydes:

| peroxide No. | starting aldehyde |
|---|---|
| 33 | dichloroacetaldehyde |
| 34 | diethylacetaldehyde |
| 35 | 2.3-dimethyl-3-hydroxypropanal |
| 36 | p-chlorobenzaldehyde |
| 37 | o-chlorobenzaldehyde |
| 7 | benzaldehyde |
| 8 | p-methoxybenzaldehyde. |

EXAMPLE VIII 14.6 g of $H_2O_2$ 70% w/w (0.3 mole) were added to a solution of 0.3 g of p-toluene sulphonic acid in 60 ml toluene and at 20° C (cooling) 27.6 g of dodecanal (0.15 mole) were added with stirring. During this addition a white precipitate was formed. Then the mixture was connected to a vacuum system, heated to 40° C and at this temperature water was slowly removed by azeotropic distillation. After 30 minutes a clear solution was formed and in 3½ hours 9 ml of water were obtained, containing 13.6% of active oxygen. The dry peroxide solution thus obtained having an AO content of 3.94% was cooled to $-10°$ C. After the precipitated crystalline material had been isolated by filtration and drying, 29.3 g of dihydroperoxyperoxide No. 38 were obtained having a melting point of 56°–58° C and an AO content of 10.7% (calculated 11.06%). Purity 97%. No other peroxides were present upon T.L.C. analysis. The I.R. spectrum showed a strong band at 3438 cm$^{-1}$ due to O—O—H.

89 g of the above peroxide No. 38 solution in toluene were washed with water containing sodiumhydrogen carbonate to acid free. 12 g of dimethyl phthalate and 12 g of methoxyethoxy ethanol (methylcarbitol) were added and then the toluene was removed under reduced pressure. A solution of peroxide N. 38 in dimethyl phthalate - methyloxitol remained with an AO content of 6.3%.

EXAMPLE IX 36 g (0.5 mole) of isobutyraldehyde were added to a mixture of 250 ml of n-butylacetate, 2.8 g of p-toluene sulfonic acid 1 aq. and 53.5 g of $H_2O_2$ 70% w/w (1.1 mole) in 15 minutes at 20° C. (cooling) with stirring. After a period of 1 hour at 20° C. the reactor was evacuated and water was slowly distilled off azeotropically at 35° C. In 3 hours 25 ml of water were removed from the reaction mixture containing about 5.6% of hydrogen peroxide.

The reaction mixture was cooled to 20° C. and subsequently the peroxide solution was washed with concentrated ammonium sulphate solution and with a 8% w/w solution of sodium hydrogen carbonate. 100 g of dimethyl phthalate and 40 g of hexylene glycol were added to the resulting solution (about 290 g) giving after removal of butylacetate by distillation under reduced pressure about 210 g of peroxide solution showing an active oxygen content of 8.0%. By T.L.C. analysis it was shown that about 85% of the AO present exists in the form of the dihydroperoxyperoxide No. 21. In an analogous way, solutions of the following peroxides were prepared, starting from various aldehydes.

| peroxide no. | starting aldehyde |
|---|---|
| 20 | n-butyraldehyde |
| 39 | phenyl acetaldehyde |
| 31 | heptanal. |

Although the invention has been described in detail for the purpose of illustration, it is to be understood that such detail is solely for that purpose and that variations can be made by those skilled in the art without departing from the spirit and scope of the invention except as it might be limited by the claims.

What we claim is:

1. A process for preparing an organic peroxidic composition, consisting essentially of a compound having the general formula

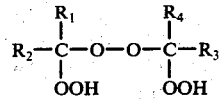

wherein $R_1$ and $R_4$ each are selected from the group consisting of hydrogen and a lower alkyl group, $R_2$ and $R_3$ may be the same or different and each is selected from the group consisting of branched alkyl group having from 1 to 12 carbon atoms, an unbranched alkyl group having from 1 to 12 carbon atoms, a branched alkyl group having from 1 to 12 carbon atoms substituted with a group selected from the group consisting of hydroxy, lower alkoxy, lower alkoxycarbonyl, halogen and phenyl, an unbranched alkyl group having from 1 to 12 carbon atoms substituted with a group selected from the group consisting of hydroxy, lower alkoxy, lower alkoxycarbonyl, halogen and phenyl; phenyl, phenyl substituted with a group selected from the group consisting of lower alkoxy and halogen, and wherein $R_1$ together with $R_2$, $R_3$ together with $R_4$ form a branched or unbranched alkylene group having a total 12 carbon atoms and 5 or 6 carbon atoms in the nucleus, and wherein $R_1$ together with $R_4$ form a lower alkylene group, comprising reacting carbonyl compounds having the formulae

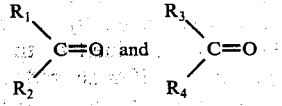

wherein the symbols $R_1$, $R_2$, $R_3$ and $R_4$ have the meanings as defined, with hydrogen peroxide in an organic solvent, which forms an azeotrope with water and wherein both the starting carbonyl compound and the peroxidic composition formed are substantially soluble, said solvent being other than the starting carbonyl compound, in the presence of an acid catalyst selected from the group consisting of mineral acids, strong organic acids, and strong acid ion exchangers, in an amount of 0.2–200 mg equivalent per mole of said carbonyl compounds, at a temperature of 10°–50° C.

while simultaneously removing water by distillation under reduced pressure.

2. The process of claim 1 wherein the carbonyl compound is a compound having the formula

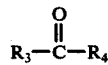

wherein $R_3$ is selected from the group consisting of alkyl radical having from 1 to 12 carbon atoms, an unbranched alkyl radical having from 1 to 12 carbon atoms, and phenyl and $R_4$ represents a group selected from the group consisting of phenyl, an alkyl radical, an alkyl radical substituted with a group selected from the group consisting of hydroxy, lower alkoxy, lower alkoxycarbonyl, benzoyl, and phenyl.

3. The process of claim 1 in which the starting carbonyl compound is a compound having the formula

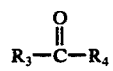

wherein $R_3$ and $R_4$ together form a branched alkylene group having a total of 12 carbon atoms and 5 or 6 carbon atoms in the nucleus.

4. The process of claim 1 in which the starting carbonyl compound is a compound having the formula

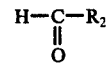

in which $R_2$ is selected from the group consisting of phenyl, phenyl substituted with a group selected from the group consisting of lower alkoxy and halogen; a branched alkyl having 1 to 12 carbon atoms, an unbranched alkyl having 1 to 12 carbon atoms, a branched alkyl having 1 to 12 carbon atoms substituted with a group selected from the group consisting of halogen, hydroxy, and phenyl, and an unbranched alkyl having 1 to 12 carbon atoms substituted with a group selected from the group consisting of halogen, hydroxy, and phenyl.

5. The process of claim 1 in which an aqueous solution of $H_2O_2$ is used having 30–85% by weight of $H_2O_2$.

6. The process of claim 1 in which the reaction mixture the molar ratio of carbonyl groups to $H_2O_2$ is between 1:1 and 1:4.

7. The process of claim 1 in which the removal of water by distillation takes place in the presence of an organic solvent which forms an azeotrope with water.

8. The process of claim 1 in which the organic solvent is selected from the group consisting of benzene, toluene, and butyl acetate.

9. The process of claim 1 which comprises increasing in the peroxidic composition the content of the compound having a formulae of claim 1 by carrying out an after-treatment with an aqueous solution of sodium sulfite.

10. The process of claim 1 wherein the organic peroxide is

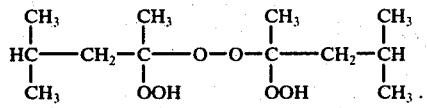

* * * * *